(12) United States Patent
Bral (10) Patent No.: US 8,657,783 B2
(45) Date of Patent: Feb. 25, 2014

(54) INJECTABLE SOLUTION CONTAINER AND SYRINGE

(75) Inventor: Pourang Bral, Passaic, NJ (US)

(73) Assignee: DentistInJerseyCity.net, Jersey City, NJ (US)

( * ) Notice: Subject to any disclaimer, the term of this patent is extended or adjusted under 35 U.S.C. 154(b) by 223 days.

(21) Appl. No.: 12/927,136

(22) Filed: Nov. 8, 2010

(65) Prior Publication Data

US 2012/0116212 A1    May 10, 2012

(51) Int. Cl.
    *A61M 5/00*    (2006.01)

(52) U.S. Cl.
    USPC .................... 604/111; 604/110; 604/246

(58) Field of Classification Search
    USPC ........ 604/22, 93.01, 112, 117, 110, 111, 118, 604/121, 131, 151–155, 173, 246, 272–274, 604/57–60, 218
    See application file for complete search history.

(56) References Cited

U.S. PATENT DOCUMENTS

| | | | |
|---|---|---|---|
| 5,259,840 A * | 11/1993 | Boris | 604/110 |
| 7,803,128 B2 * | 9/2010 | Christensen et al. | 604/65 |
| 2001/0049510 A1 * | 12/2001 | Burr et al. | 604/272 |
| 2007/0185470 A1 * | 8/2007 | Steinbach et al. | 604/500 |
| 2007/0197968 A1 * | 8/2007 | Pongpairochana et al. | 604/131 |
| 2008/0009824 A1 * | 1/2008 | Moberg et al. | 604/500 |

* cited by examiner

*Primary Examiner* — Jason Flick
*Assistant Examiner* — Leah Stohr (57) ABSTRACT

A container of an injectable solution is disclosed herein including various sensors, electrodes, a memory device, and other features that monitor the process of extraction or injection of the content of the container to ensure it is completed successfully in an automated manner, such as in an automatic injecting device.

16 Claims, 8 Drawing Sheets

INJECTABLE SOLUTION CONTAINER AND SYRINGE

STATEMENT REGARDING FEDERALLY SPONSORED RESEARCH OR DEVELOPMENT

Not Applicable

THE NAME OF THE PARTIES TO A JOINT RESEARCH AGREEMENT

Not applicable.

INCORPORATION-BY-REFERENCE OF MATERIAL SUBMITTED ON A COMPACT DISC

Not Applicable

BACKGROUND OF THE INVENTION

In the U.S. patent application Ser. No. 12/590,658, an injection device 1 was disclosed that would reduce or prevent the pain associated with injection, and surgical procedures such as puncture, incision, or otherwise violation of the skin barrier, using electrical and physical stimulation, simultaneously or consecutively, of the area of the skin or mucosa in the vicinity of the injection, puncture, incision, or otherwise violation of the skin or mucosa barrier. In this application, various components of said injection device 1 are disclosed. Furthermore, a container 18 of injectable solution is also disclosed with improved characteristics.

BRIEF SUMMARY OF THE INVENTION

A container of injectable solution and a syringe is disclosed that includes sensors and various components to help proper administration of injection by an automated injecting device.

DETAILED DESCRIPTION OF THE INVENTION

Reference is made to U.S. patent application Ser. No. 12/590,658, filed on Nov. 12, 2009 to establish the priority date for various aspects of the following invention.

In a specific example of the invention, a container of injectable solution 18 is disclosed, including a plurality of ports 27 made for example of rubber. Said plurality of ports 27 are penetrable by a needle of a syringe (not shown) to extract its contents 25, FIG. 5. Said container 18 has a plurality of flexible areas 23 that can be forced to move outwards out of or inwards into said container 18 depending on increased or decreased pressure, respectively, inside said container 18. The first advantage of this design is to relatively equilibrate the pressures inside and outside of said container 18 during extracting the contents 25. Since extracting the contents 25 creates a relative vacuum inside said container 18, it would increasingly become difficult to extract the contents 25 as the contents 25 are emptied unless the vacuum is filled. In order to do so, said plurality of flexible areas 23 expand inward due to relatively higher outside pressure, filling the vacuum, and facilitating further extraction of said contents 25 from said container 18. In a preferred example of the invention, before extraction of the contents 25, a fluid such as a gas is injected into said container 18 through said plurality of ports 27, inflating said plurality of expandable areas 23. This method facilitates extraction of more of said contents 25 before encountering a strong enough vacuum to hamper proper extraction of said contents 25.

Figure 1:
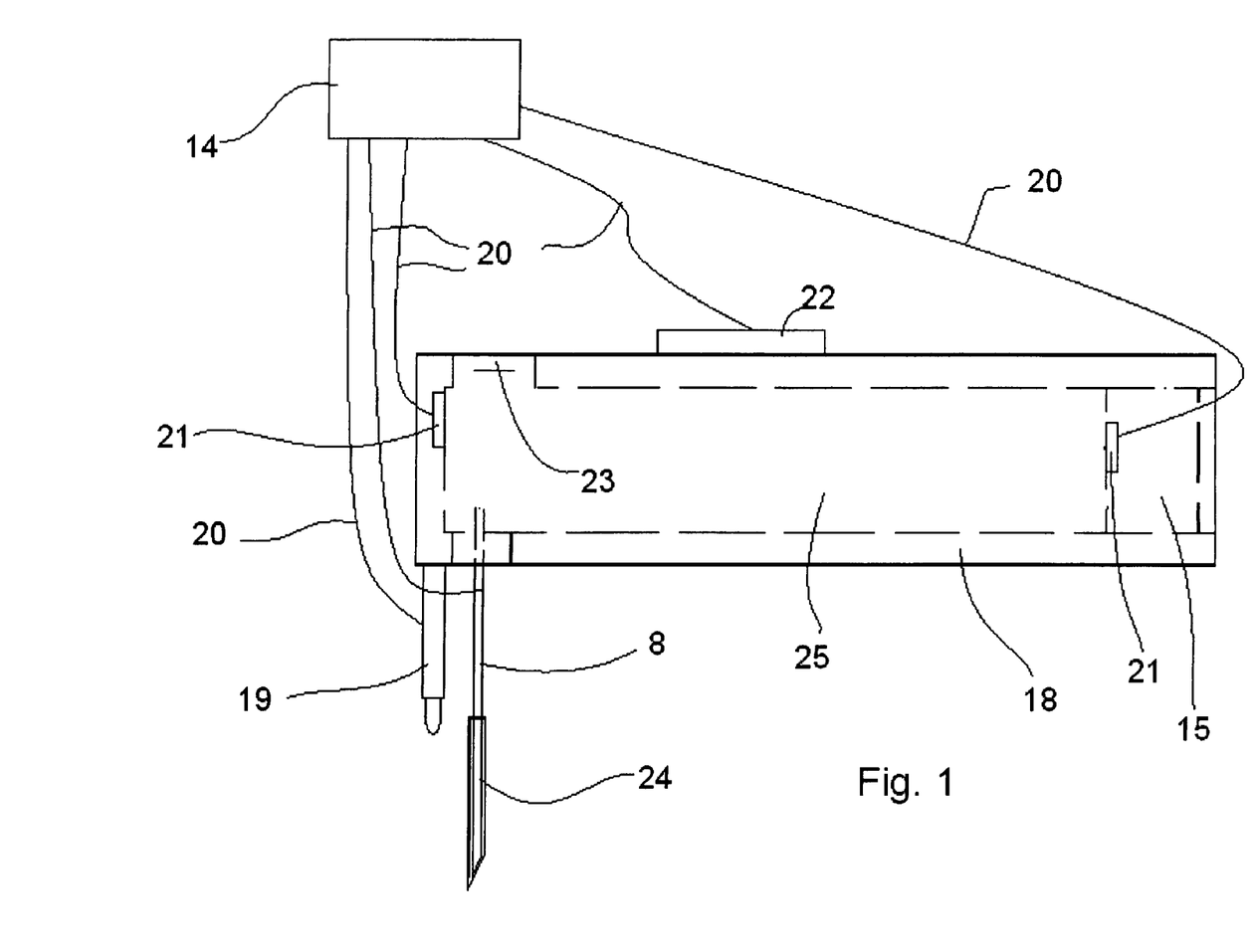
FIG. 1 shows a container of injectable solution including a memory device, electrodes, a needle, and an electrical switch connected to a processor. It also shows various components of a preferred embodiment of a container of injectable solution.

In a specific example of the invention, said injecting device 1 includes means to automatically apply electric and physical stimulation to the area of injection, actuate the penetration of a plurality of needles 8 into the recipient's skin, and injection of the contents 25 of said plurality of containers 18, through said plurality of needles 8, using various motors to actuate different steps, a processor 14 to control, guide, and time these steps, and various sensors to ascertain successful completion of each step, FIG. 1.

Figure 2:
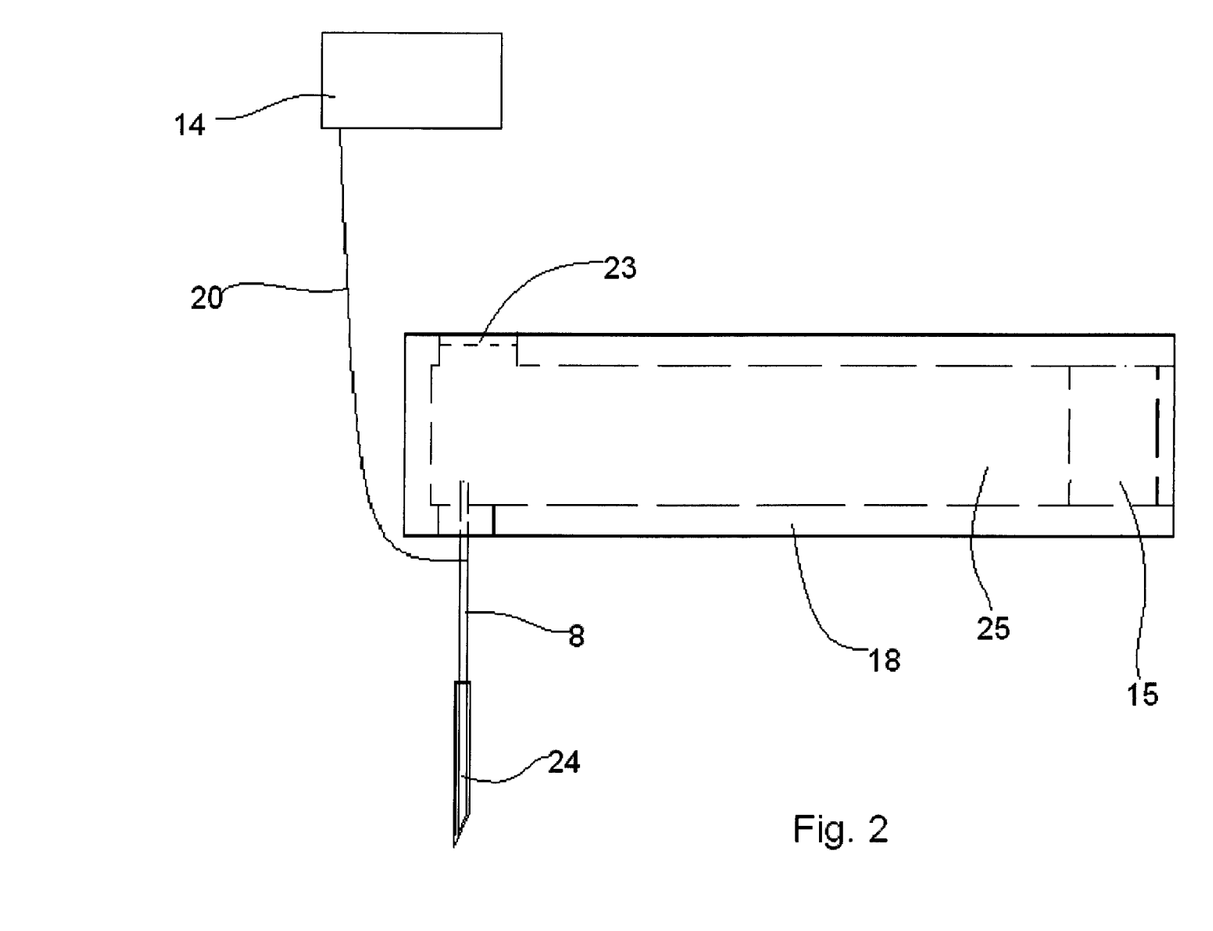
FIGS. 2 & 3 show how a flexible area inflates when a plunger pushes the contents towards the needle and the adjacent flexible area.
Figure 3:
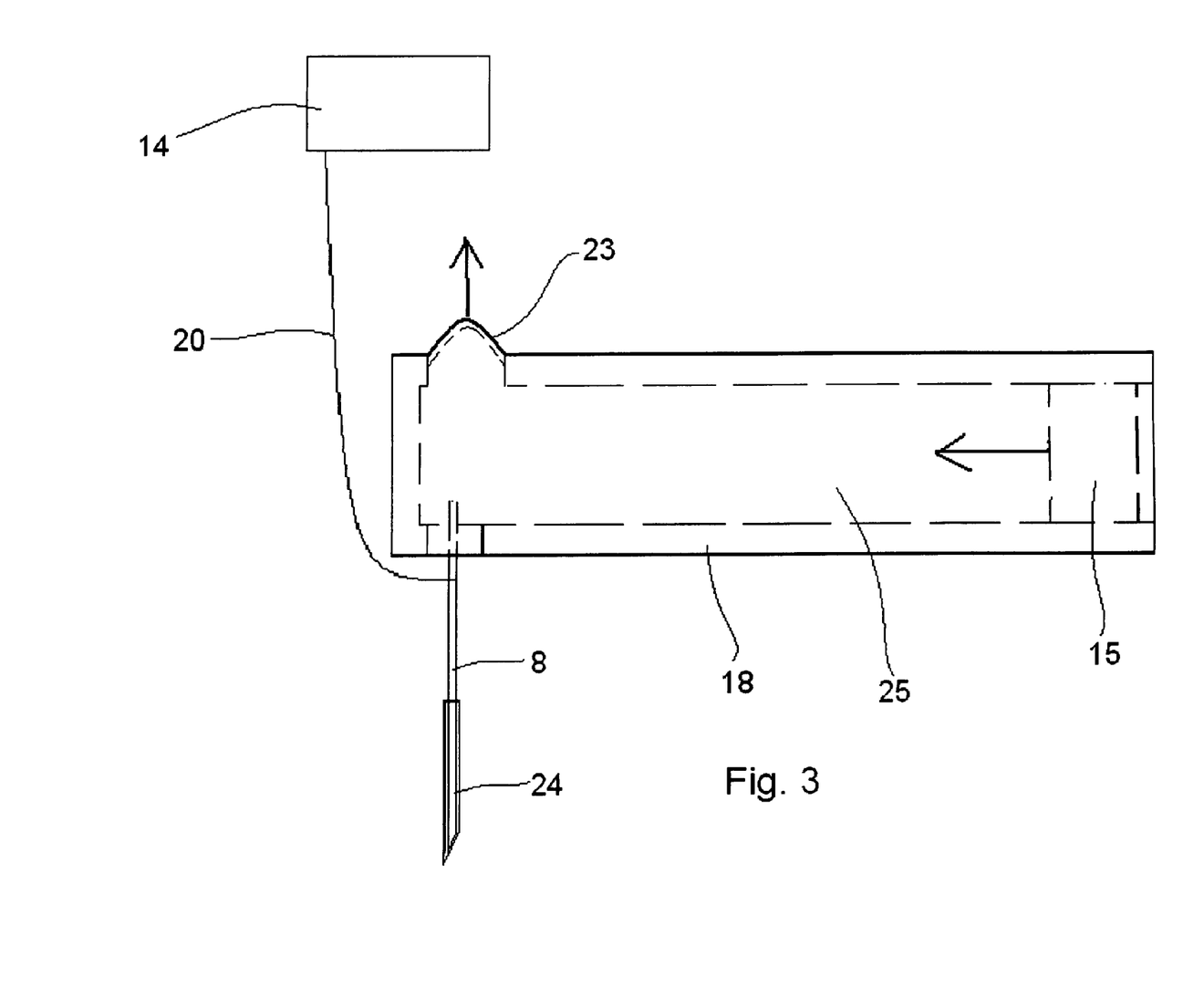

In a specific example of the invention, this design is used to assure that said container 18 has no cracks and that the process of extraction of said contents 25 is carried out properly. When injecting gas into said container 18 or extracting said contents 25 therefrom, the pressure inside said container 18 changes relative to the outside pressure. This will lead to expansion of said plurality of flexible areas 23 outwards from or inwards into said container 18. This will indicate proper content 25 extraction from said container 18, because if, for any reason, said contents 25 were not extracted, said plurality of flexible areas 23 would not expand into said container 18. This advantage becomes more apparent when the extraction is performed automatically by said injecting device 1. Since visual verification of proper content extraction from said container 18 may not be feasible, the expansion of said plurality of flexible areas 23 with change of pressure inside said container 18 proves to be a reliable indicator of successful content 25 extraction from said container 18. A sensor (not shown) inside said injecting device 1 can be used to detect inward or outward expansion of said plurality of flexible areas 23, relay this message to said processor 14 which will in turn allow the extraction process to proceed, FIGS. 2 and 3.

In a specific example of the invention, said plurality of flexible areas 23 lose their expansion capacity after a period of time. That period of time can be made to coincide approximately with the expiration date of said contents 25 of said container 18. Therefore, at the expiration date of said contents 25, said plurality of flexible areas 23 do not expand as a response to a change in pressure inside said container 18. The sensor inside said injecting device 1 does not detect any inward or outward expansion of said plurality of flexible areas 23, no message is relayed to said processor 14 which will in turn not allow the extraction process to proceed. This can act as a safety mechanism to avoid injection of expired contents 25 to the recipient.

Figure 6A:
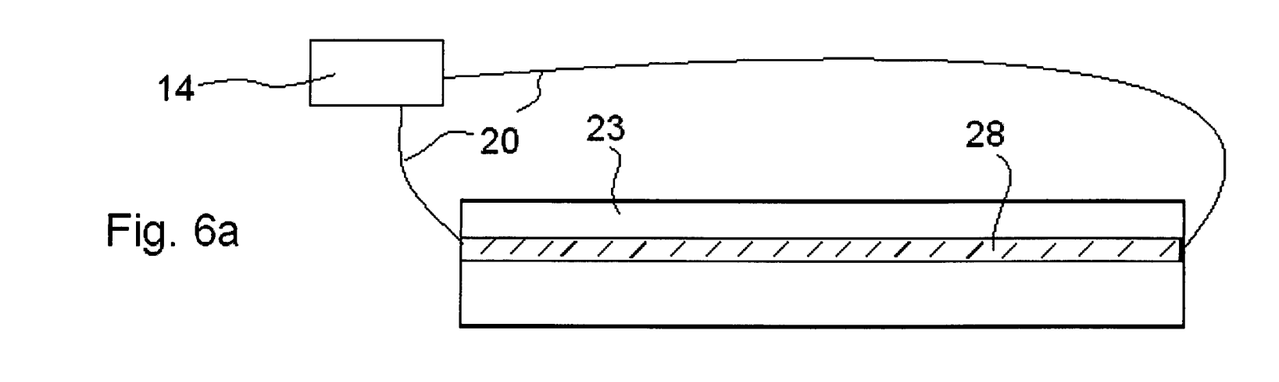
FIGS. 6a & 6b show how a flexible area breaks an electrically conductive means when it inflates or deflates.
Figure 6B:
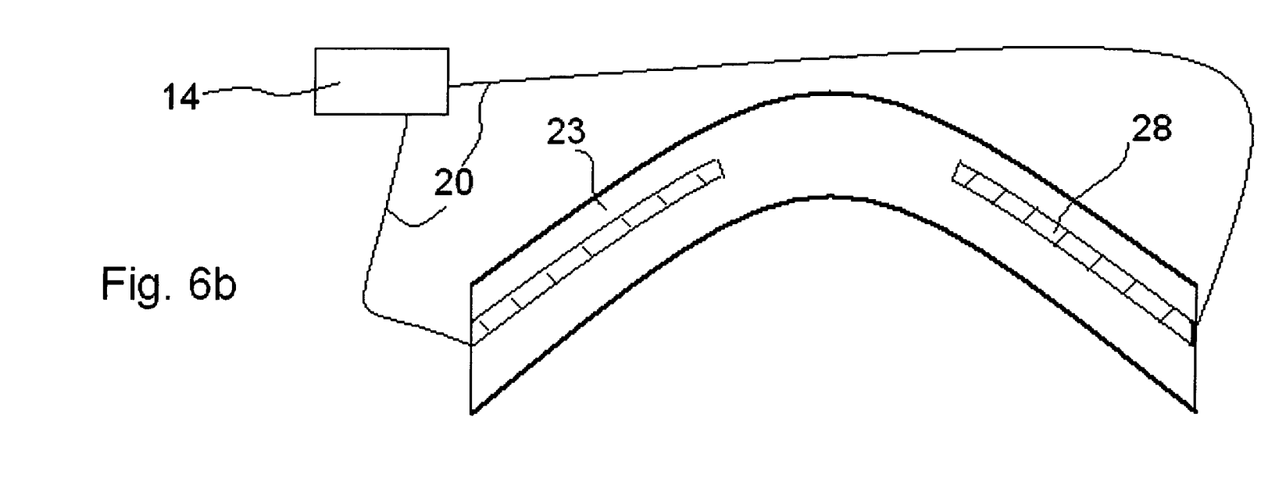

In a specific example of the invention, a plurality of electrically conductive means 28 is in contact with, adhered to, or preferably embedded in, said plurality of flexible areas 23, FIG. 6a. Said plurality of electrically conductive means 28 are rather delicate and not as expandable or flexible as said plurality of flexible areas 23. Furthermore, said plurality of electrically conductive means 28 are electrically connected to said processor 14 that detects its continuity as long as an electric current can pass through said plurality of electrically conductive means 28. When said plurality of flexible areas 23 expand enough, said plurality of electrically conductive means 28, in contact with, adhered to, or embedded in said plurality of flexible areas 23, are physically torn apart and are no longer electrically conductive, FIG. 6b. This design can be used to ascertain said container 18 is used only once, thereby preventing abuse by, for example, recreational drug users attempting to reuse said container 18. When said container 18 comes in contact with said injecting device 1 in order to initiate extraction of its contents 25, said processor 14 detects whether or not said plurality of electrically conductive means 28 are broken. If so, it does not allow the process of said content 25 extraction to proceed as one of the steps necessary for a successful content 25 injection into a recipient.

Figure 5:
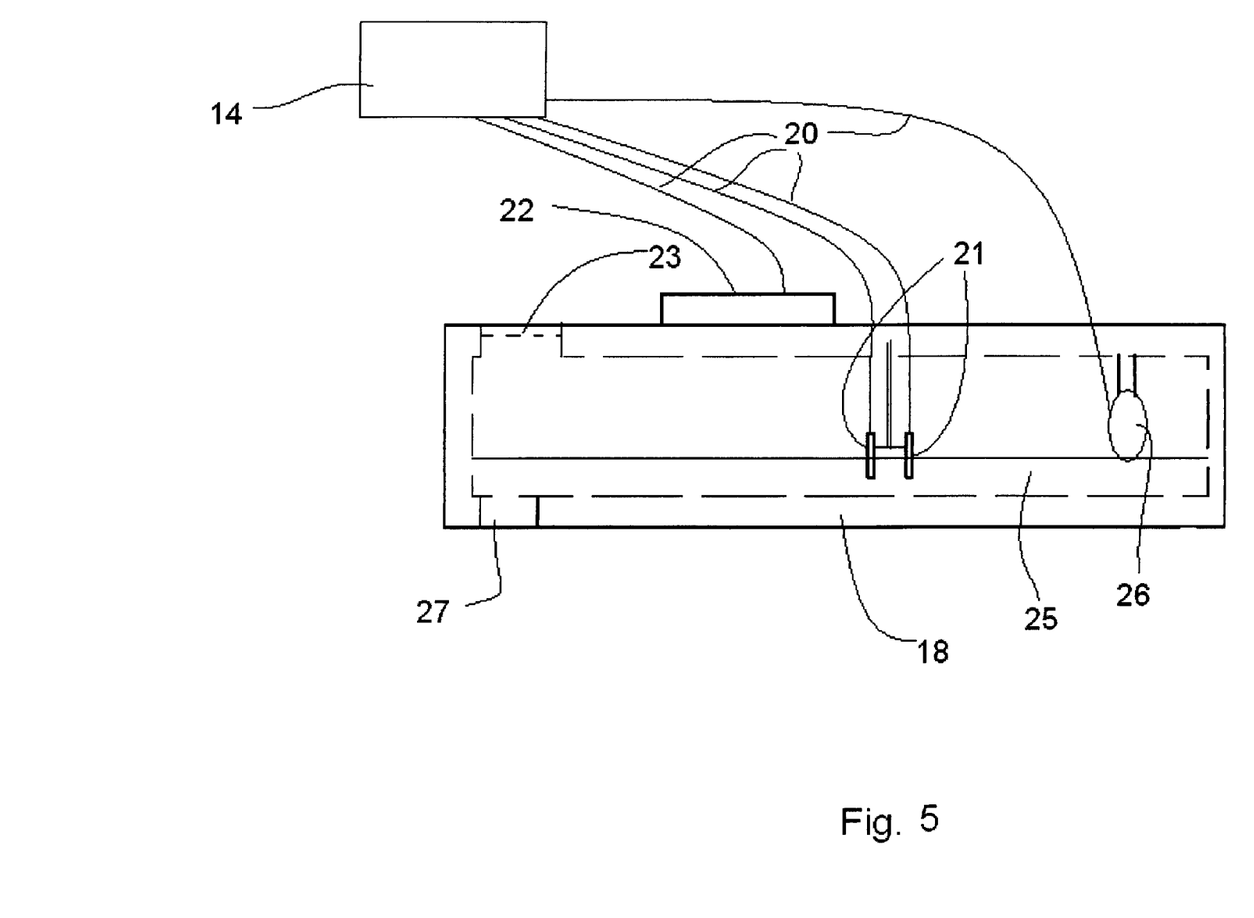
FIG. 5 illustrates a container of injectable solution including a plurality of electrodes, a barometer, and a memory device.

In a specific example of the invention, a barometer is placed inside said container 18 to detect and relay any change in pressure inside said container 18 to said processor 14 to evaluate the success of extraction of said contents 25 from said container 18, FIG. 5.

In another example of the invention, said container 18 includes a plurality of electrodes 21 being in electric contact with said content 2, electrically connected to said processor 14, and placed on the walls of and/or inside said container 18, FIG. 5. Said content 25 is electrically conductive, though it may exhibit a significant electrical resistance to an electrical current passing through it. Before extracting said content 25, said processor 14 sends a signal to at least one said electrode 21. If there is enough said content 25 in said container 18, the electric signal passes through said electrically conductive content 25 to at least one other electrode 21 and back to said processor 14, indicating of availability of adequate said content 25 for injection. Then, extraction of said content 25 may proceed. In case of inadequate said content 25 in said container 18, not enough said content 25 is there to carry an electrical signal from at least one said electrode 21 to another, and no signal is received by said processor 14, which in turn will not allow the extraction of said contents 25 to proceed or at least will warn of inadequate supply of said content 25.

In another example of the invention, said container 18 includes a memory device 22 that stores certain electrical characteristics that the contents 25 of said container 18 have, for example, the electrical resistance that the contents 25 exhibit when two or more said electrodes 21 are placed a certain distance apart from each other, FIG. 5. Two or more said electrodes 21 are placed on the walls of or inside said container 18 and in contact with its contents. This setup allows measuring the electrical resistance inherent in the content 25 of said container 18. Said processor 14 will then verify that the measured electrical resistance of the contents 25 matches the electrical resistance stored by the manufacturer in said memory device 22 in said container 18 before it permits the injection to proceed. This design should prove beneficial in preventing abuse of the injecting device 1, for example, by recreational drug users. Since the electrical characteristics of a recreational drug, that is filled in said container 18 after the original contents are emptied, are likely to be different than those of the original contents of said container 18, said processor 14 will prevent the injection to proceed.

In a specific example of the invention, said container 18 is connected or connectable to a needle 8 with an inside canal 29 through which said contents 25 can pass to a said needle 8 tip that can reach and enter the recipient's body, FIG. 1.

In a specific example of the invention, a plurality of said containers 18 can be held securely inside and released from said injection device 1 at will.

In a specific example of the invention, said plurality of containers 18 are generally shaped like a tube that contains a liquid. A plunger 15 is so positioned in said container 18 as to be able to force the liquid contents 25 towards and into said needle 8, FIG. 1.

In a specific example of the invention, said container 18 has a relatively elongated shape. Said container of injectable solution 18 has the capacity to receive and secure a plurality of said needles 8 so that the length of said plurality of needles 8 is generally perpendicular to the length of said container 18. This design helps prevent spillage of said medicine from said cartridge due to shaking, vibration, and/or otherwise movement of said plurality of containers of injectable solution 18 and their contents, FIG. 1.

The electrical environment inside the body is different than that outside the body. For example, the resistance to an electrical current passing through the body is different than that outside the body. In the following example of the invention, use is made of this phenomenon to ascertain successful needle penetration through the skin and into the body before said content 25 of said container of injectable solution 18 is ejected out of said plurality of needles 8. A plurality of said needles 8 are at least partially electrically conductive and electrically connected to said processor 14 that senses any change in the electrical environment of said plurality of needles 8, FIG. 1. Said plurality of containers of injectable solution 18 are designed to accept said plurality of needles 8. When said injecting device 1 is activated, it actuates said plurality of needles 8 to penetrate the skin and enter the body of the recipient. When said processor 14 senses the electrical environment at said plurality of needles 8 resembles the electrical environment inside the body, it sends a signal to initiate the injection of the contents of said plurality of containers 18.

In a specific example of the invention, a portion of said plurality of needles 8 is electrically insulated 24, FIG. 1. That portion may include a span of said plurality of needles 8 starting from the tip of said needle 8 to a designated distance towards where said needle 8 meets said container of injectable solution 18. This design assures that said needle 8 has penetrated the skin a designated distance before said processor 14 senses a change in the electrical environment by said needle 8. Therefore said processor 14 senses a successful penetration of said needle 8 into the recipient's skin only after said needle 8 has penetrated into the skin a designated distance. It is only then that said processor 14 sends the signal that injection of the contents of said cartridge can start. Since there is limited or no pain perception associated with the injection, this safety mechanism is important because it ascertains that said needle 8 has penetrated the recipient's skin by a designated length, and the life saving contents of said container of injectable solution 18 are injected properly and not wasted outside the recipient's skin.

In a specific example of the invention, the content of said container of injectable solution 18 is electrically conductive. A plurality of electrodes 21 are placed on the walls of or inside said container of injectable solution 18 and/or said plunger 15, and are in electrical contact with the contents 25 of said container of injectable solution 18, FIG. 1. The electrically conductive content 25 of said container of injectable solution 18 can transfer electrical impulses between, for example, one of the plurality of said needles 8 and a plurality of said electrodes 21. This design can be applied, for example, to obviate the difficult task of attaching an electrical wire 20 directly to a plurality of said needles 8 in order to electrically connect them to said processor 14. Instead, said electrical wire 20 can conveniently be electrically connected to a plurality of said electrodes 21. Upon successful penetration of said plurality of needles 8 into the recipient's body, an electrical impulse signaling a change in the environment of said plurality of needles 8 travels from said plurality of needles 8 into the contents 25 of said container of injectable solution 18 and to said plurality of electrodes 21. From there, an electrical wire 20 transfers the electrical impulse to said processor 14.

In a specific example of the invention, said container of injectable solution 18 has the following safety mechanism to ensure that the process of extraction of said contents 25 is carried out properly and that the contents of said container 18 do not spill out useless through a defect or a fracture in the walls of said container 18. Said container 18 walls includes a plurality of flexible areas 23 that are in contact with the inside pressure of said container 18 from the inside and are exposed to the outside of said container 18 from the outside, FIG. 2. When said plunger 15 pushes the contents of said container of injectable solution 18 towards a plurality of said needles 8 during the process of injection, the pressure in the contents increases provided there are no fractures on the walls of said cartridge and the only exit available to the contents of said cartridge is through said plurality of needles 8. The inside pressure increases because said content 25 cannot escape through said needle 8 as readily due to the small size of the canal 29 inside said needle 8. This increase in pressure will, in turn, force said plurality of flexible areas 23 to bulge out while the contents are under pressure and exiting said plurality of needles 8, FIG. 3. The bulge in said plurality of flexible areas 23 activates a sensor (not shown) to send a signal to said processor 14 which in turn sends a signal to said injecting device 1 to continue the process of injection. If there is a fracture in any of the walls of said container of injectable solution 18, the increase in pressure in the contents during the process of injection will be minimal or nonexistent. There will be minimal or no bulging on said plurality of flexible areas 23 Said injection device 1 will not be activated; and the process of injection will be discontinued to avoid spillage and waste of the contents of said container of injectable solution 18. The recipient is notified of the failure of injection so he can procure the life-saving medicine in a different manner.

Figure 4:
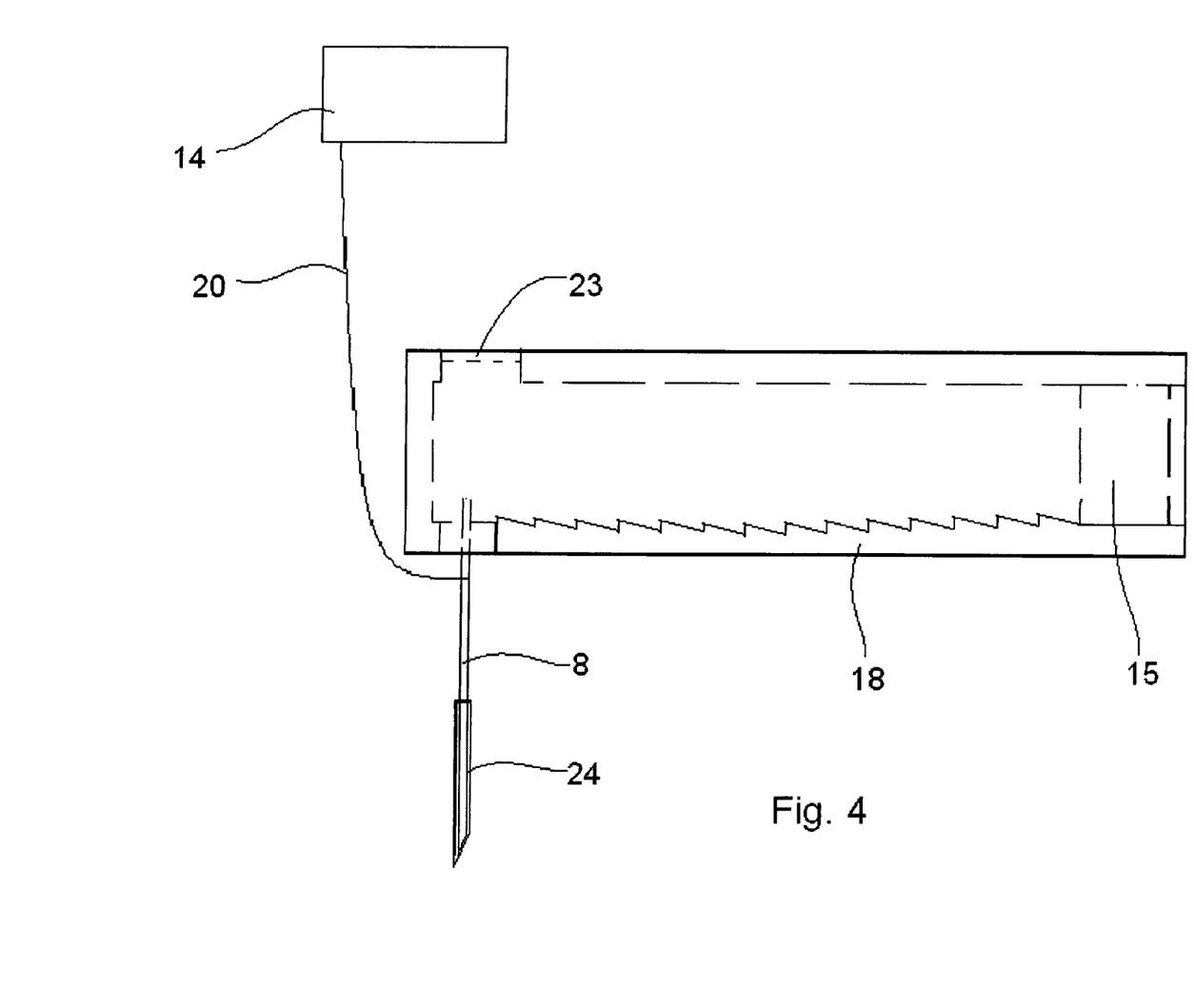
FIG. 4 depicts a container of injectable solution including a means to allow the plunger to move only in one direction.

In a specific example of the invention, said container of injectable solution 18 has the following safety mechanism to make it difficult, if not impossible, for anyone to refill said container of injectable solution 18. This safety mechanism can be implemented, for example, to prevent recreational drug users to use said injecting device 1 as a conduit to abuse drugs. Said container of injectable solution 18 is designed to have a general shape of a tube, in which said plunger 15 can travel to press the contents 25 of said container of injectable solution 18 into and out of said plurality of needles 8. At least part of the inner surface of said container of injectable solution 18 is shape to allow the travel of said plunger 15 towards said plurality of needles 8, but not in the opposite direction, FIG. 4.

In a specific example of the invention, said container of injectable solution 18 includes a plurality of electric switches 19, located preferably near said needle 8, and electrically connected to said processor 14, FIG. 1. Said plurality of electric switches 19 are so positioned that as said needle 8 penetrates the recipient's body, said plurality of electric switches 19 get closer to the recipient's skin. At a designated distance from the skin, said plurality of electric switches 19 signal to said processor 14 indicating that said needle 8 has penetrated a designated distance into the recipient's body and the process of injecting said contents 25 can begin. Said processor 14 in turn allows the injection to proceed. Since there is limited or no pain perception associated with the injection, this safety mechanism is important in order to ascertain that said needle 8 has penetrated the recipient's skin by a designated length, and the life saving contents of said container of injectable solution 18 are injected properly and not wasted outside the recipient's skin.

Figure 7:
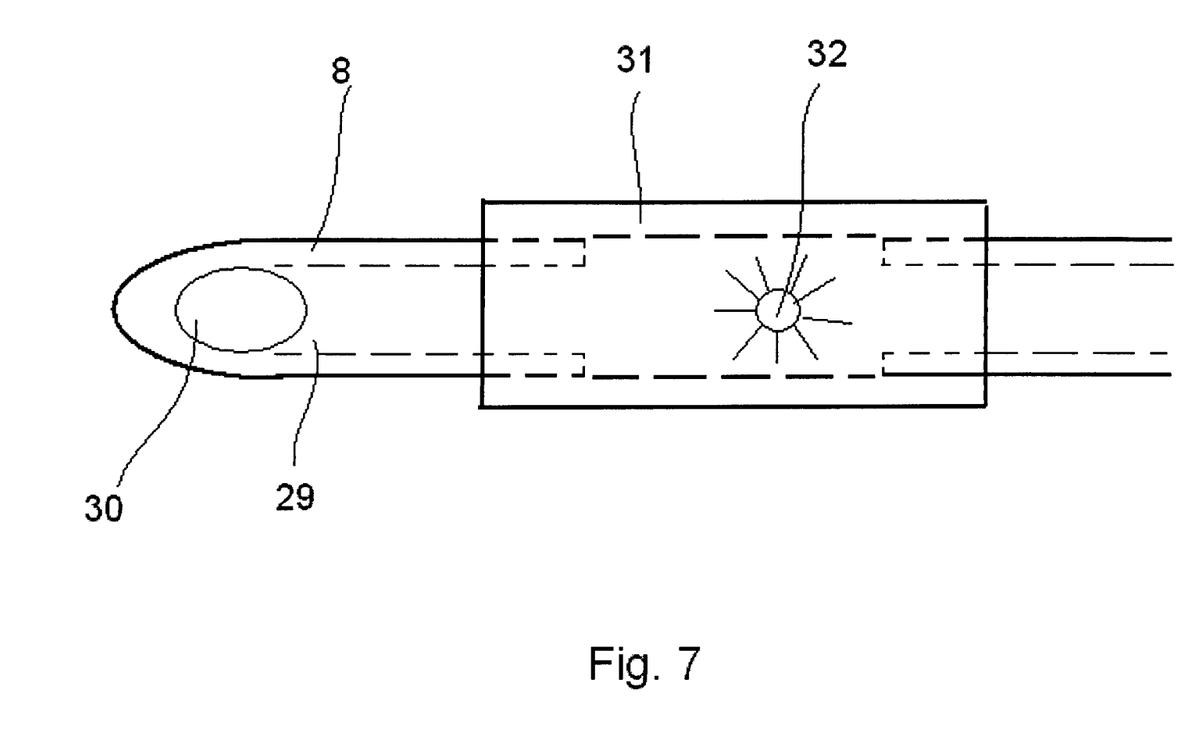
FIG. 7 illustrates a needle including a tip, a canal, a segment with a larger canal, and a semi-pervious object placed in the larger canal.

In general, the size of a canal is inversely proportional to the speed of the fluid that travels inside it. In a specific example of the invention, use is made of this phenomenon to construct a backflow preventing mechanism to prevent blood and body fluids to travel through said needle 8 to said container 18 as in the following. Said needle 8 includes a plurality of segments, at some distance from said needle's 8 tip 30, with a larger inside canal 31 than said canal 29 in the rest of said needle 8, FIG. 7. Backflow of blood and other body fluids from the recipient's body occur because of a momentary higher pressure in the body than inside said container 18. If injection is administered at the correct site, said needle 8 does not pierce a major blood vessel and any backflow of blood through said needle 8 is rather limited and travels rather slowly. The presence of a plurality of segments of said needle 8 with said larger canal 31 hampers the progression of blood towards said container 18 as it takes longer to fill up said needle 8 segment with said larger canal 31 with blood. Before blood has a chance to reach said container 18, said needle 8 is removed from the recipient's body. Therefore, the flow of blood to said container 18 is prevented. This design is helpful in situations where said container 18 has enough content 25 for two or more injections; and it is preferable not to introduce blood or other body fluids into said contents. In a specific example of the invention, a semi-pervious material 32 such as a sponge or bristles of a brush is placed inside said plurality of larger canals 31 to retard the free flow of fluids inside said plurality of larger canals 32, in order to further help prevent the backflow of blood into said container 18.

In a specific example of the invention, said container has the general shape of a tube and includes a content 25 with some electrical resistance. A plurality of electrodes 21 are placed at a certain distance from each other, and are in electrical contact with said content 25 and with said processor 14. Said container 25 is positioned with respect to the gravity in such a way that the more said content 25 is there in said container 18, the more said content 25 is in contact with said plurality of electrodes 21, FIG. 5. It is also known that the more said content 25 is contact with said plurality of electrodes 21, the less electrical resistance is felt between said plurality of electrodes 21. This fact can be used to measure the amount of said content 25 in said container 18.

Figure 8:
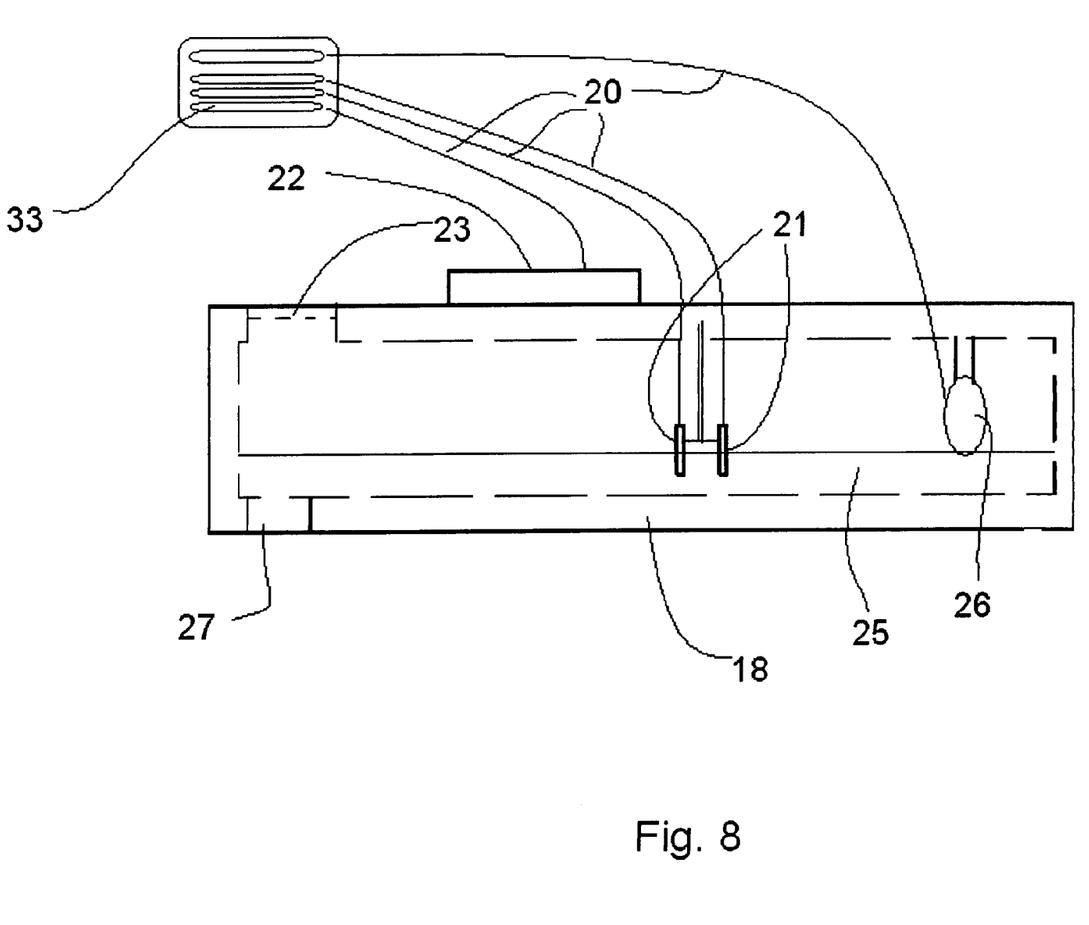
FIG. 8 shows a container including a plurality of wires that are attached to a plurality of connectors.

In a specific example of the invention, a plurality of said wires 20 are not directly connected to said processor 14. Instead, they are connected to a plurality of connectors 33 that can in turn be connected to said processor 14, FIG. 8.

One skilled in the art will appreciate that the present invention can be practiced by other than the described embodiments, which are presented here for purposes of illustration and not of limitation, and the present invention is limited only by the claims that follow.

What I claim is:

1. A container of injectable solution including a needle with a canal through which the content of said container can pass, and a plunger that pushes said content of said container towards the general direction of said needle which leads to the outside of said container; said needle being electrical conductive and connected or connectable to a processor that senses when the electric environment of said needle has changed and resembles that of inside a recipient's body in which case it signals of a successful said needle penetration into a recipient's body, said container further includes I) a content that is electrically conductive even though it may have a high electrical resistance, and a plurality of electrodes being in electric contact with said content, electrically connected or connectable to said processor, in order to ascertain availability of adequate said content before the process of infection of said content begins, and II) a memory device that stores certain electrical characteristics displayed by said contents of said container, being electrically connected or connectable to said processor that compares the electrical characteristics of said content as obtained through said plurality of electrodes to those contained in said memory device to assure said content is the original content contained in said container.

2. A container of injectable solution according to claim 1 including one or more flexible areas that are exposed to the pressure of the inside of said container from the inside and are exposed to the outside environment from the outside and that can be forced outwards out of said container or inwards into said container depending on the pressure inside said container being higher or lower, respectively, than the outside pressure.

3. A container of injectable solution according to claim 2 that is meant for one-time use whose said content is forced out by an automated device, said container including a said one or more flexible areas at least part of which is in contact with, adhered to, or surrounding at least a part of one or more electrically conductive means 1) that are not as flexible or expandable as said one or more flexible areas, and 2) that furthermore are electrically connected or connectable to a processor that monitors the physical continuity of said one or more electrically conductive means which can be broken when said one or more flexible areas move inwardly or outwardly enough to break said one or more electrically conductive means which will then fail to conduct the electric current transmitted by said processor indicating that said container has been used once and not to be used again.

4. A container of injectable solution according to claim 1 including one or more electrical switches, electrically connected or connectable to said processor, and preferably positioned near said needle so that as said needle penetrates the recipient's skin, said one or more electric switches get closer to the recipient's skin, which at a designated distance from the recipient's skin, signal of successful penetration of said needle to said processor which in turn allows the injection to proceed.

5. A container of injectable solution according to claim 1 in which said needle has a segment with a larger inside canal than the canal inside generally the rest of said needle to hamper the backflow of blood and other body fluids through said canal from the recipient's body into said container.

6. A container of injectable solution according to claim 5 including one or more semi-pervious substances that are placed inside said larger canal to further retard the backflow of blood and other body fluids through said canal into said container.

7. A container of injectable solution according to claim 1 including one or more flexible areas that can move outwards out of, or inwards into, said container depending on the pressure inside said container being higher or lower, respectively, than the outside pressure.

8. A container of injectable solution according to claim 7 that is meant for one-time use whose said content is forced out by an automated device, said container including a said one or more flexible areas at least part of which is in contact with one or more electrically conductive means that are not as flexible or expandable as said one or more flexible areas, and that furthermore are electrically connected to a processor that monitors the physical continuity of said one or more electrically conductive means which can be broken when said one or more flexible areas expand by deflating inwardly or inflating outwardly enough to break said one or more electrically conductive means which will then fail to conduct the electric current transmitted by said processor indicating that said container has been used once and not to be used again.

9. A container of injectable solution, including a plurality of ports through which said injectable solution can be extracted through a canal of a needle that can penetrate said plurality of ports, said container further including a plurality of flexible areas that are exposed to the pressure of the inside of said container from the inside and are exposed to the outside environment from the outside and that can be forced to move outwards out of said container or inwards into said container depending on the pressure inside said container being higher or lower, respectively, than the outside pressure, said container designed for one-time use whose contents are extracted by an automated device, said container including one or more electrically conductive means that 1) are not as flexible or expandable as said one or more flexible areas, 2) at least part of which is in contact with, adhered to, or is surrounded by at least part of said one or more flexible areas and 3) are electrically connected or connectable to a processor that monitors the physical continuity of said one or more electrically conductive means which can be broken when said one or more flexible areas move inwardly or outwardly enough to break said one or more electrically conductive means which will then fail to conduct the electric current transmitted by said processor indicating that said container has been used once and not to be used again.

10. A container of injectable solution according to claim 9 including a content that is electrically conductive even though it may have a high electrical resistance, and two or more electrodes that are in electrical contact with said content and electrically connected or connectable to a processor that determines the availability of adequate said content before the process of extraction of said content can begin.

11. A container of injectable solution according to claim 9 including 1) a memory device that stores certain electrical characteristics exhibited by said content of said container, and 2) two or more electrodes that are placed in electrical contact with said content in order to measure said contents electrical properties; said memory device and said plurality of electrodes being electrically connected or connectable to a processor that compares the electrical characteristics of said content as obtained through said plurality of electrodes to those contained in said memory device to assure said content is the original content contained in said container.

12. A container of injectable solution according to claim 9 in which said automated device is an injecting device that would reduce or prevent the pain associated with injection, puncture, incision, or otherwise violation of the skin barrier such as a surgical procedure, using electrical and physical stimulation, simultaneously or consecutively, of the area of the skin or mucosa in the vicinity of the injection, puncture, incision, or otherwise violation of the skin or mucosa barrier.

13. A container of injectable solution including a content that is electrically conductive even though it may have a high electrical resistance; a port through which said content can be extracted through a canal of a needle that can penetrate said port; a plurality of electrodes being in electric contact with said content and electrically connected or connectable to a processor, in order to determine availability of adequate said content before the process of extraction of said content begins; and one or more flexible areas that are exposed to the pressure of the inside of said container from the inside and are exposed to the outside environment from the outside and that can move outwards out of or inwards into said container depending on the pressure inside said container being higher or lower, respectively, than the outside pressure.

14. A container of injectable solution according to claim 13 that is meant for one-time use whose contents are extracted by an automated device, said container including said one or more flexible areas at least part of which is in contact with, adhered to, or surrounds at least one part of one or more electrically conductive means that are not as flexible or expandable as said one or more flexible areas, and that furthermore are electrically connected or connectable to a processor that monitors the physical continuity of said one or more electrically conductive means which can be broken when said one or more flexible areas move inwardly or outwardly enough to break said one or more electrically conductive means which will then fail to conduct the electric current transmitted by said processor indicating that said container has been used once and not to be used again.

15. A container of injectable solution according to claim 14 in which said automated device is an injecting device that would reduce or prevent the pain associated with injection, a surgical procedure such as puncture, incision, or otherwise violation of the skin barrier, using electrical and physical stimulation, simultaneously or consecutively, of the area of the skin or mucosa in the vicinity of the injection, puncture, incision, or otherwise violation of the skin or mucosa barrier.

16. A container of injectable solution according to claim 13 including a memory device that stores certain electrical characteristics exhibited by said content, being electrically connected or connectable to said processor that compares the electrical characteristics of said content as obtained through said plurality of electrodes to those contained in said memory device to assure said content is the original content contained in said container.

* * * * *